United States Patent

Hosoi et al.

[11] Patent Number: 5,541,002
[45] Date of Patent: Jul. 30, 1996

[54] INK JET PRINTING PAPER

[75] Inventors: Kiyoshi Hosoi; Tsukasa Matsuda, both of Ebina, Japan

[73] Assignee: Fuji Xerox Co., Ltd., Tokyo, Japan

[21] Appl. No.: 322,329

[22] Filed: Oct. 13, 1994

[30] Foreign Application Priority Data

Dec. 27, 1993 [JP] Japan ..................... 5-330371

[51] Int. Cl.⁶ .............. B32B 29/00; G03G 7/00
[52] U.S. Cl. ............ 428/537.5; 428/331; 428/332; 428/340; 428/913; 428/447; 428/448; 428/513; 162/135
[58] Field of Search ....................... 428/331, 332, 428/340, 913, 513, 447, 448, 537.5

[56] References Cited

U.S. PATENT DOCUMENTS 4,482,628 11/1984 Katsura et al. ............... 430/538
4,645,736 2/1987 Anthonsen et al. ............ 430/538

FOREIGN PATENT DOCUMENTS

62-202781 9/1987 Japan.
2-192984 7/1990 Japan.

*Primary Examiner*—P. C. Sluby
*Attorney, Agent, or Firm*—Oliff & Berridge

[57] ABSTRACT

A printing paper comprises a paper substrate and a coating layer formed on at least one side of the substrate and formed from a coating composition comprising a white pigment and a water-soluble resin in an amount of from 4 to 10 g/m². When the paper sheet is divided or split into a printing surface layer and a non-printing surface layer, a difference in shrinking rate along a cross direction between the printing surface layer and the non-printing surface layer is within a range of ±0.1%. The paper can suppress curling on printing.

14 Claims, 5 Drawing Sheets

INK JET PRINTING PAPER

BACKGROUND OF THE INVENTION

1. Field of the Invention

This invention relates to a paper sheet for ink jet printing which is adapted for use in ink jet printing systems using aqueous inks and which is unlikely to curl when printed and ensures high-quality print images thereon.

2. Description of the Related Art

For ink jet printing paper on which aqueous inks are applied, there are known ones which are suited for obtaining high-quality images and which have a coating layer by coating, onto a printing surface thereof, a coating composition comprising major proportion of a white pigment such as silica and an water-soluble resin. As is known, this type of printing paper can be divided into two classes including one wherein a large amount of a coating composition is applied onto the print side so that the ink is predominantly absorbed in the coating layer and the other class wherein a coating layer is formed in such a small amount that the ink is absorbed in both the coating layer and a paper substrate.

With the printing paper having a great amount of the coating, most of the ink is kept in the coating layer, so that a substantial dimensional change takes place between the coating layer and the substrate owing to the swelling through the water absorption of the water-soluble resin in the coating layer and owing to the shrinkage through the dehydration of the resin, thereby causing the paper to be considerably curled. On the other hand, with the printing paper whose coating layer is formed in a small amount, the ink infiltrates not only into the coating layer, but also into the inside of the substrate. This eventually leads to the dimensional change of the substrate through water absorption and dehydration of the fibers in the substrate, thereby causing the paper to be considerably curled or to become rugged.

Japanese Patent Laid-open No. Sho 62-202781 proposes an improvement of a printing paper having a great amount of the coating thereon wherein in order to suppress the curling, an ink-receiving layer is formed on a substrate having two or more layers and thus, the basis weight of the printing paper is made as great as 120 to 500 g/m$^2$.

However, the technique set out in this gazette has the problem in practical application that the printing paper has such a great basis weight that it becomes too stiff or is in heavy body. This results in too high a buckling force of the paper at the time of its feed, thus presenting a problem on travellability such a miss feed especially for small-sized printers.

With respect to the printing paper having a coating layer in a small amount, the Japanese Patent Laid-open No. Hei 2-192984 proposes an improvement wherein a paper substrate is arranged as having a high surface smoothness, on which a coating layer is formed so that the resultant recording sheet has a water absorption within a given time greater than a predetermined level thereby avoiding rugged or curling defects on absorption of water.

However, in the improvement set forth in the Japanese Patent Laid-open No. Hei 2-192984, the water absorption of the substrate is set as being higher than a predetermined level, so that its ink absorptivity becomes high. This presents another problem that the ink readily arrives at the back side of the substrate, with a kind of setoff being undesirably conspicuous.

SUMMARY OF THE INVENTION

It is accordingly an object of the invention to provide a printing paper for ink jet printing which is substantially free of any problem on curling after printing although it has a coating layer formed in a relatively small amount of 4 to 10 g/m$^2$ and which has high strength of the coating layer.

It is another object of the invention to provide a printing paper for ink jet printing which is unlikely to be curled or rugged after printing and thus, ensures print images with a high color clarity and a good resolution.

It is a further object of the invention to provide a printing paper for ink jet printing which is low in production costs.

We have made intensive studies on a printing paper sheet for ink jet printing which has a reduced degree of curling after printing and ensures print images of high quality. As a result, it has been found that with a printing paper which is coated thereon in a small amount particularly within a range of 4 to 10 g/m$^2$, curling takes place as follows. Now, it is assumed that the printing paper is considered as being divided into two halves along the thickness thereof. One includes a print surface layer, which covers substantially from a center line of the total thickness of the printing sheet including, in combination, the coating layer and a substrate to the coating layer surface on which an image is printed. The other includes a non-printing surface layer at the opposite side of the sheet. In this condition, curling is ascribed to the difference between the printing surface layer and the non-printing surface layer with respect to the shrinkage caused by the variations in moisture in the respective layers and particularly, to the difference between the shrinking rates of the respective layers along the cross direction (CD) (i.e. a direction normal to a direction of the fibers aligned in the paper substrate).

More particularly, we have assumed that the shrinkage of the printing paper takes place by virtue of the infiltration of water into the substrate from an ink and subsequent dehydration. Under this assumption, studies have been made on a method for suppressing, to a minimum, curling of printing paper after printing. In a printing paper which has a relatively reduced amount of a coating thereon within a range of 4 to 10 g/m$^2$, the curling after printing on a paper sheet is most greatly influenced by the difference in the shrinking rate along the CD direction between the printing surface layer and the non-printing surface layer at the time of changing from conditions of a temperature of 20° C. and a relative humidity of 90% to conditions of a temperature of 20° C. and a relative humidity of 25%. When the difference in the shrinking rate is within ±0.1%, the curling after printing can be suppressed to a minimum.

Accordingly, the above objects can be achieved, according to the invention, by a printing paper which comprises a substrate and a coating layer formed on at least one side of the substrate and formed from a coating composition comprising a white pigment and a water-soluble resin in an amount of from 4 to 10 g/m$^2$, wherein when the paper sheet is divided or split into a printing surface layer and a non-printing surface layer as defined hereinbefore, a difference in shrinking rate along a cross direction (CD) between the printing surface layer and the non-printing surface layer is within a range of ±0.1%.

For attaining the difference within a range of ±0.1%, the paper substrate should preferably have an orientation ratio of the fibers between the machine direction (MD) (i.e. a direction of fibers being aligned or a running direction of a paper-making machine) and the cross direction (CD) of not greater than 1.35:1 when measured according to a ultrasonic propagation rate method. Alternatively, a water-soluble resin which may be contained in a coating composition to be applied onto a printing surface side of the printing paper sheet may be applied to the non-printing surface so that the difference in the shrinking rate along the cross direction between the printing surface layer and the non-printing surface layer is within a range of ±0.1%.

DETAILED DESCRIPTION AND EMBODIMENTS OF THE INVENTION

The substrate used in the printing paper of the invention is generally made of a paper sheet which is constituted primarily of wood pulp. If necessary, glass fibers and synthetic fibers may be blended with the wood pulp. The substrate is usually formulated with fillers. Examples of the filler include white pigments such as heavy or precipitated calcium carbonate, talc, kaolin, clay, titanium dioxide, zeolites, white carbon, mixtures thereof and the like. In order to increase voids or spaces in the substrate and to increase an ink absorption, the filler is used in an amount of from 3 to 30 wt %, preferably from 5 to 20 wt %. The use of the filler in amounts greater than 30 wt % is unfavorable because the substrate significantly lowers in strength and dust generates considerably.

The substrate generally has an apparent density of 0.70 to 0.90 g/cm$^3$, preferably from 0.75 to 0.85 g/cm$^3$. If the apparent density is smaller than 0.70 g/cm$^3$, a coating composition is liable to infiltrate into the inside thereof, so that the resultant coating layer becomes thin, with a tendency toward the uneven coating concentration. In addition, the resin component in the coating composition infiltrates into the substrate, with a lowering in strength of the coating layer. On the contrary, when the apparent density exceeds 0.90 g/cm$^3$, the contact area among the fibers becomes so great that the substrate is apt to suffer an influence of expansion and contraction exerted thereon. This leads to the problem that a substantial degree of curling after printing, with the attendant problem that the absorption rate of an ink becomes so low that color mixing and bleeding will result.

The substrate is made in such a way that it usually has a basis weight of 50 to 100 g/m$^2$, preferably from 60 to 90 g/m$^2$ and a thickness of 65 to 150 μm, preferably 80 to 140 μm. If the basis weight is less than 50 g/m$^2$, the setoff is liable to occur with a great degree of curling after printing. On the contrary, when the basis weight exceeds 100 g/m$^2$, the substrate becomes stiff with an undesirable increase of buckling force. This may bring about the trouble on feed through printers. Likewise, when the thickness is smaller than 65 μm, the setoff is more liable to occur. When the thickness exceeds 150 μm, the paper substrate becomes so stiff that the buckling force increases, thus being liable to invite a feed trouble in printers.

The coating composition which is coated on at least one side of the substrate should comprise a white pigment and a water-soluble resin.

The white pigment should preferably have a BET specific surface area ranging from 100 to 400 m$^2$/g and an average particle size of 2 to 15 μm. When the BET specific surface area is less than 100 m$^2$/g, the ink absorption capacity of the coating layer unfavorably lowers, thus color mixing and bleeding being apt to occur. On the contrary, when the BET specific surface area is greater than 400 m$^2$/g, the hardness lowers to provide a very soft pigment, making it difficult to write with a pencil or the like. When the average particle size of a pigment is smaller than 2 μm, writing with a pencil or the like is difficult. On the contrary, over 15 μm, the coating layer has a substantial irregular surface and an ink flows towards recessed portions. This is disadvantageous in that when printed, a uniform shape of ink dots cannot be obtained, resulting in the uneven ink concentration along with the occurrence of color mixing and bleeding.

The most preferred white pigment includes, for example, amorphous silica although not limited thereto. The white pigment is formulated in the coating composition in an amount of from 50 to 85 wt %, preferably from 60 to 80 wt %. When the amount is smaller than 50 wt %, an adverse influence is produced as in the case where the BET specific surface area of pigment is smaller than 200 m$^2$/g. On the contrary, when the amount exceeds 85 wt %, the strength of the coating layer lowers. Accordingly, dust is apt to come off and writing with a pencil or the like writing utensils becomes difficult.

When used as the white pigment, amorphous silica may be modified on the surfaces thereof with metallic cations such as Ca, Al, Mg and the like in order to improve waterproofing, light fastness and the like. Moreover, if desired, pigments having a BET specific surface area smaller than 100 m$^2$/g may be formulated in small amounts.

The water-soluble resins formulated in the coating composition include polyvinyl alcohol derivatives such as fully saponified polyvinyl alcohol, partially saponified polyvinyl alcohol, silanol group-modified vinyl alcohol copolymers and the like, cellulose derivatives such as carboxymethylcellulose, hydroxyethyl cellulose, hydroxypropylmethyl cellulose and the like, and water-soluble polymers such as polyvinyl pyrrolidone, oxidized starch, modified starch, gelatin, casein and the like. These may be used singly or in combination. Of these, the modified polyvinyl alcohols such as fully saponified polyvinyl alcohol, partially saponified polyvinyl alcohol, silanol group-modified vinyl alcohol copolymers and the like are preferred in view of the strength of the resultant coating layer. Moreover, the silanol group-modified vinyl alcohol copolymers are most preferred because the strength of the coating layer is more improved and it is possible to increase the amount of a pigment in the layer which serves to catch a dye in an ink.

For the purpose of imparting waterproofing to an aqueous ink image formed on the surface of a coating layer, the composition may further comprise amine polymers such as polyethyleneimine, polyacrylamine salts and the like and quaternary salts thereof, cationic water-soluble polymers such as copolymers of acrylic compounds and ammonium salts, and water-soluble metals. These may be used singly or in combination. If necessary, fluorescent brighteners, surface active agents, mildewproofing agents, dispersants and the like may be further added to the composition.

The printing paper of the invention is formed by coating at least one side of a substrate as stated hereinabove with the coating composition in an amount of from 4 to 10 g/m², preferably from 5 to 8 g/m². If the amount is less than 4 g/m², the fibers of the substrate appear in the coating layer and causes uneven infiltration of an ink. As a consequence, the formation of ink dots with a uniform diameter is not possible, resulting not only in an uneven concentration but also in the degradation of color developing properties and the degradation of resolution. On the other hand, when the amount exceeds 10 g/m², the strength of the coating layer lowers. The coating may be carried out by various types of coaters such as reverse coaters, air knife coaters, blade coaters, gate roll coaters and the like.

As stated hereinbefore, the printing sheet of the invention should have a coating layer formed in an amount of from 4 to 10 g/m² and should have a difference in shrinking rate along the cross direction between the printing surface layer and the non-printing surface layer within a range of ±0.1%.

The term "printing surface layer" is intended to mean a portion ranging from a center of the total thickness of the printing paper including the substrate and the coating layer to the surface of the coating layer. The term "non-printing surface layer" is intended to mean a portion which ranges from a center of the total thickness of the printing paper including the substrate and the coating layer to the surface of a side opposite to the side of the printing surface layer.

The term "shrinking rate" used herein means a dimensional variation rate which occurs when a substrate is subjected to dehumidification from a relative humidity of 90% R.H. to 25% R.H. at a temperature of 20° C. The difference in the shrinking rate means a value which is obtained by separating a printing paper sheet into two halves substantially at a center along the thickness thereof, i.e. a printing surface layer and a non-printing surface layer, measuring a shrinking rate of the respective layers and subtracting the value of the shrinking rate of the non-printing surface layer from that of the shrinking rate of the printing surface layer.

For controlling the difference in the shrinking rate between the printing and non-printing surface layers within a range of ±0.1%, there are used several methods. In one of such methods, when paper is made, a JET/WIRE ratio (the ratio between the pulp jetting speed and the paper-making machine wire speed) is properly controlled. Another method is one wherein the tension of a paper web along the machine direction is appropriately controlled when pressed and dried in dryers so that the fiber orientation ratio of the substrate is controlled at a predetermined level of not higher than 1.35, preferably not higher than 1.30, when determined according to a ultrasonic wave propagation rate method. In an alternative method, a substrate is coated with on one side thereof to form a printing surface layer, followed by coating either a similar coating composition as used to form the coating layer or a water-soluble resin which may be used as one component of the coating composition, onto a side opposite to the printing surface layer.

There is particularly described a process for making a paper web or substrate which has a fiber orientation ratio of not larger than 1.35 when determined by a ultrasonic wave propagation rate method.

The paper substrate is made according to a paper-making process as shown in FIGS. 3(a) to 3(f).

Figure 3A:
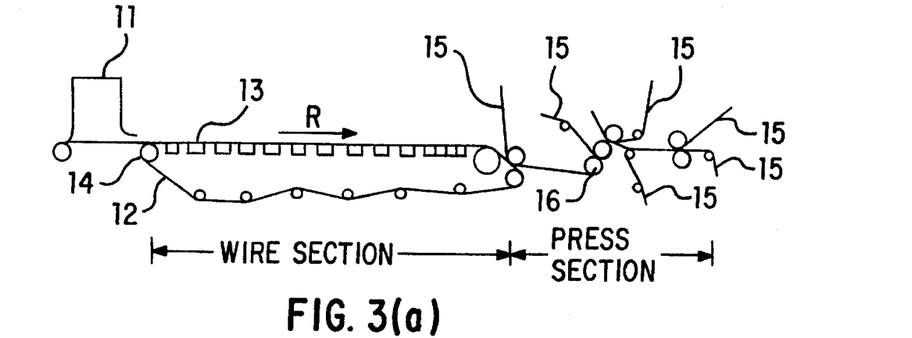
FIGS. 3(a) to 3(f) are, respectively, a schematic illustrative view of a paper making process from which a paper web suitable for the invention is made.
Figure 3B:
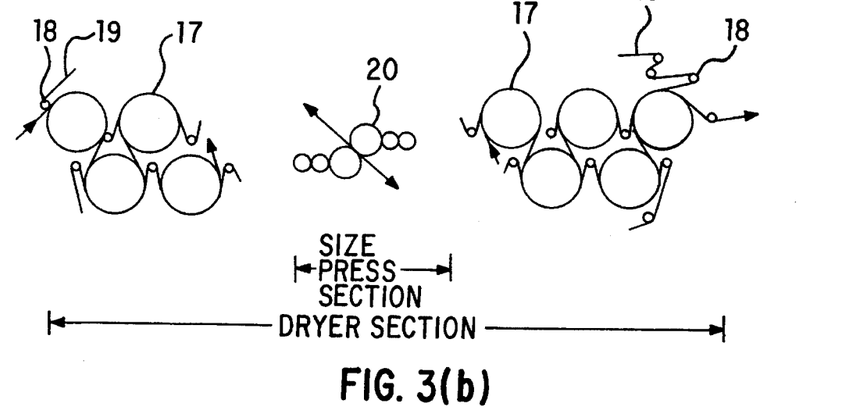
Figure 3C:
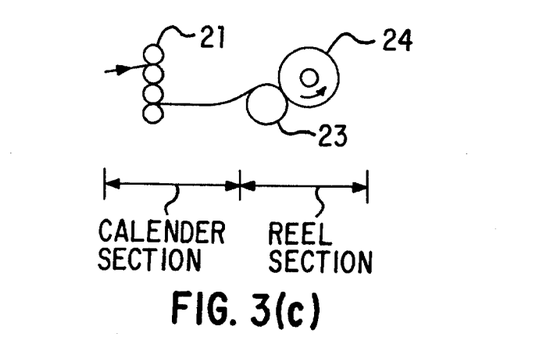

FIGS. 3(a) to 3(c) generally show a paper-making process using a Fourdrinier machine. In FIGS. 3(a) to 3(c), there are shown stock inlet 11, wire 12, hydrowheels 13, wire rolls 14, felt 15, felt rollers 16, dryer rollers 17, felt rolls 18, felt 19, size press roller 20, calender rollers 21, reel 23 and coiling roller 24.

Figure 3D:
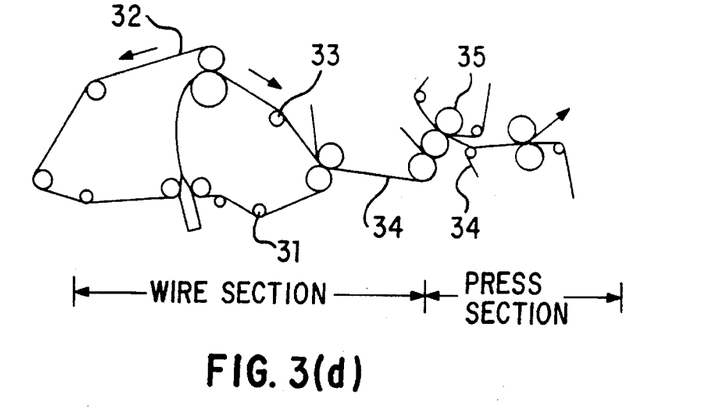
Figure 3E:
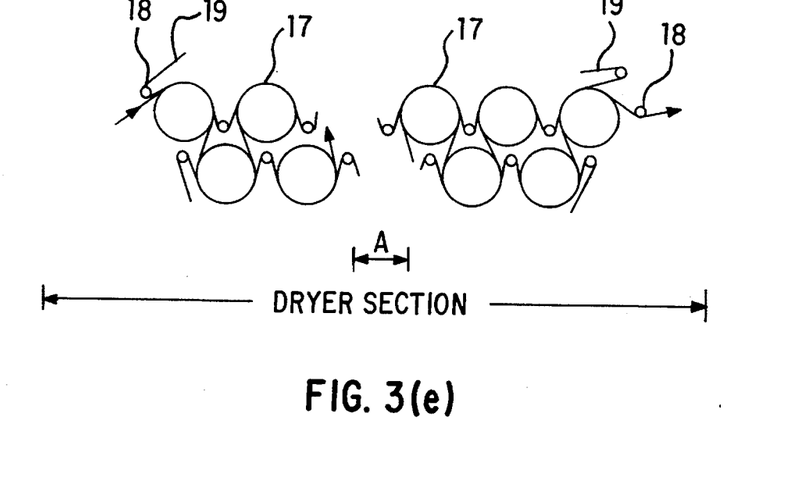
Figure 3F:
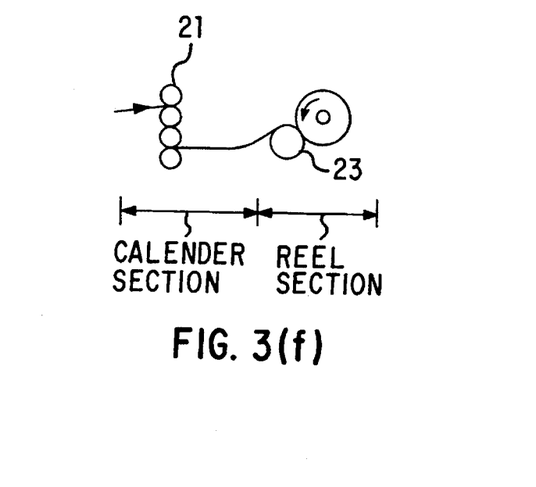

FIGS. 3(d) and 3(e) schematically show an embodiment of the invention wherein a paper-making process using a twin-wire type machine is shown. In FIGS. 3(d) and 3(e), there are shown stock inlet 31, wire 32, wire rollers 33, felt 34 and felt rollers 35. In these figures, like reference numerals indicate like parts or members as in FIGS. 3(a) and 3(b). FIG. 3(f) shows a calender section and a reel section, like FIG. 3(c).

Figure 4A:
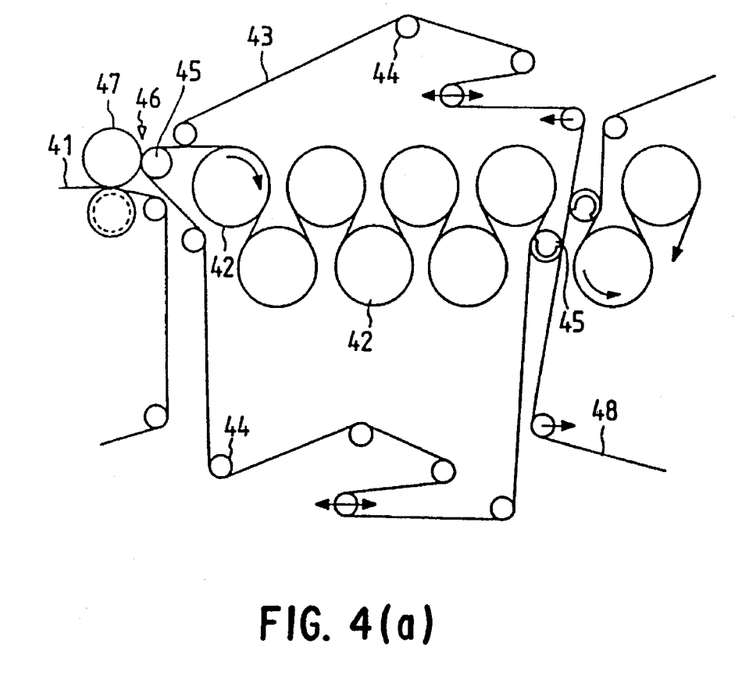
FIGS. 4(a) and 4(b) are, respectively, a schematic illustrate view showing a dryer section adapted for use in the paper-making process illustrated in FIGS. 3(a) to 3(f).
Figure 4B:
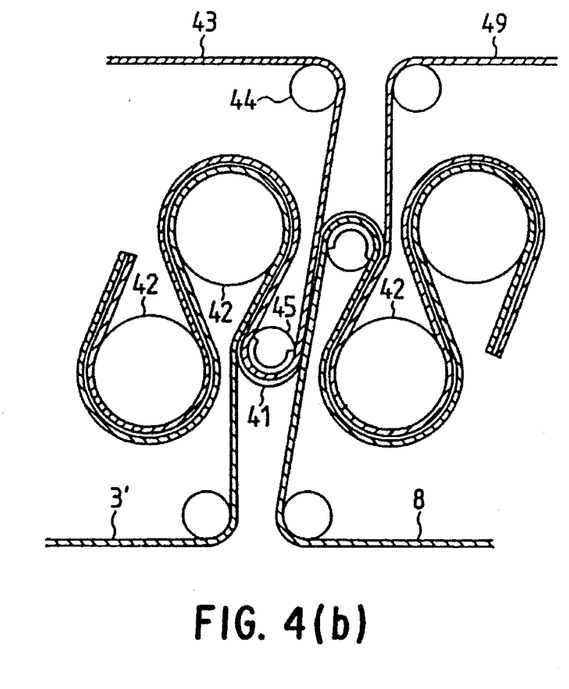

FIGS. 4(a) and 4(b), respectively, show a dryer section to realize drying of a paper web or substrate under appropriate conditions with respect to the force of constraint. In these figures, there are shown paper web 41, dryer rolls 42, felt 43, felt rolls 44, suction rolls 45, doctor 46 and last press 47.

The paper web is prepared by suitably beating raw pulp and adding mixed size agents, fillers, dyes and etc., so as to provide a pulp suspension.

In a wire section, the pulp suspension is injected toward the moving wires 12 or 32 from the stock inlet 11 or 31. At the time, a T/Y ratio, which will be defined hereinafter, is appropriately changed by controlling both a feed jet speed of the pulp suspension and a wire speed. In the wire section, a substantial amount of water in the suspension is dehydrated. Fine fibers and fillers flow out during the dehydration. With the Fourdrinier machine, the dehydration takes place only at one side thereof, which permits a compositional difference to occur at opposite sides of the paper web. Therefore, it is better to use a paper-making machine which allows dehydration from the opposite sides (e.g. a twin wire type machine and the like).

In the press section, the paper web is further dehydrated by pressing between felts 15 and felt rollers 16.

In the dryer section, the paper web is dried by application of heat between felt rolls 18 and dryer rollers 17. As shown in FIGS. 4(a) and 4(b), by means of reducing no force time period of constraint to the paper between dryer rolls 42 (that is, a drying process having a narrow distance between the dryer rolls), it is able to reduce the degree of drying under tension.

Finally, in the size press section, surface sizing agent and electric resistance adjusting agent are coated, followed by passage through calender section, reel section and shredder section to obtain a paper sheet.

Since the shrinkage of paper has relation to the longitudinal wave propagation velocity ratio and the degree of drying under tension, the shrinkage can be reduced by reducing the ratio and the degree. When the JET/WIRE ratio is appropriately controlled in the wire section of the paper-making process, the shrinkage can be reduced to a level of 0.45% or below. In this connection, if the paper web is subjected to the dryer section under the force of constraint to the paper, the shrinkage can be reduced more easily.

Accordingly, the difference in the shrinking rate as defined in the present invention can be achieved, without resorting to a specific kind of raw pulp, in accordance with predetermined paper-making conditions so that the longitudinal waves of ultrasonic wave are allowed to propagate at a velocity ratio of 1.1 to 1.5 and the paper is dried under tension to 0.1% and below.

Further, we have found that the difference in the shrinking rate along the CD direction between the two layers of the paper within the afore-defined range can be attained more easily by forming the paper sheet when the dehydration is performed from both the opposite sides of a paper web under the conditions set forth hereinbefore.

The fiber orientation ratio of the paper substrate which is determined according to the ultrasonic wave propagation rate method is a value which is obtained by dividing a ultrasonic wave propagation rate of a substrate along the machine direction (MD) by a ultrasonic wave propagation rate of the substrate along the cross direction (CD) and is expressed by the following equation Fiber orientation ratio (T/Y) of substrate by the ultrasonic wave propagation rate=(ultrasonic wave propagation rate along the machine direction)/(ultrasonic wave propagation rate along the cross direction).

Figure 1:
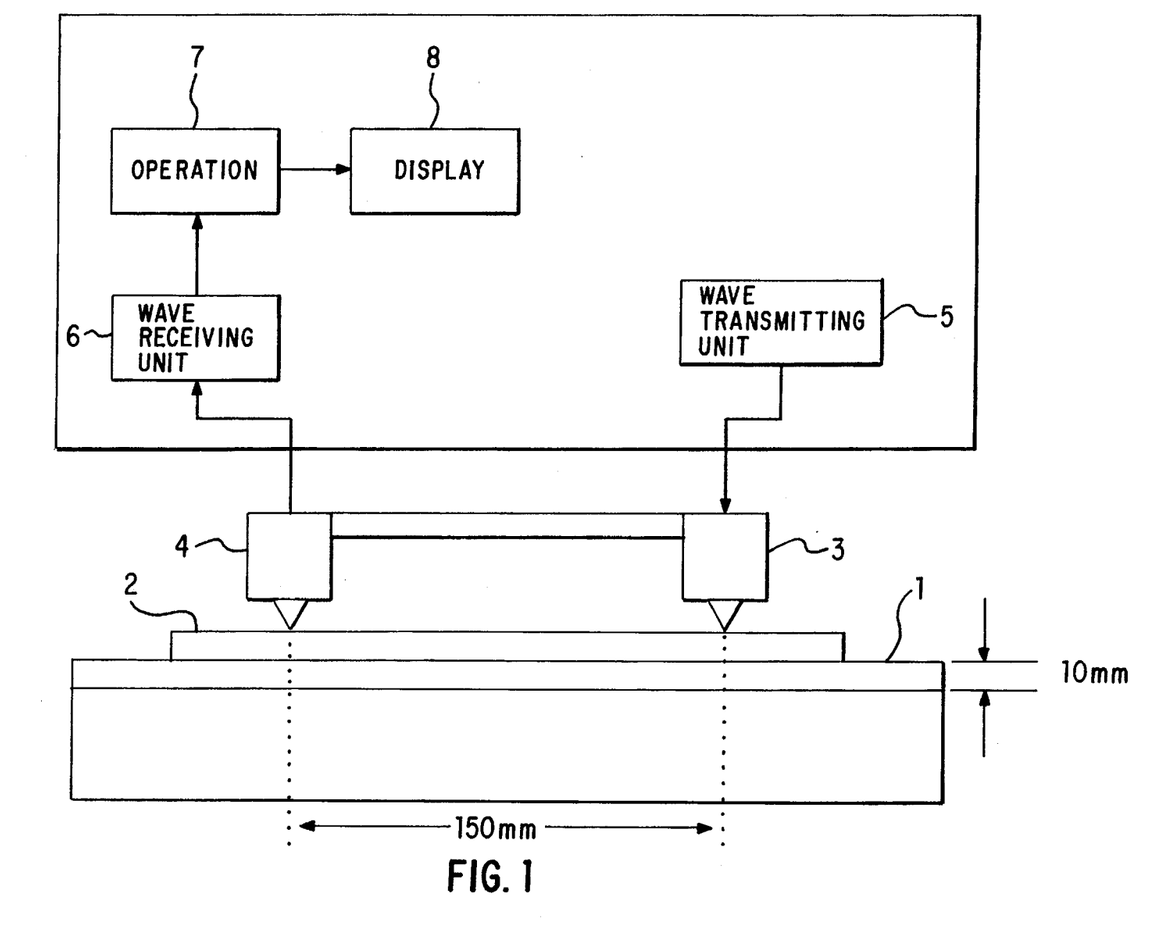
FIG. 1 is an illustrative view showing a measuring device for measuring a fiber orientation ratio according to a ultrasonic wave propagation rate method.

In practice, the fiber orientation ratio determined by the ultrasonic wave propagation rate method can be determined by a measuring method, for example shown in FIG. 1.

A sample 2 is placed on a 10 mm thick foamed rubber sheet 1, on which a wave transmitting vibrator 3 connected to a wave transmission unit 5 and a wave-receiving vibrator connected to a wave receiving unit 6 are placed such that the vibrators 3 and 5 are kept at a distance of 150 mm. The longitudinal wave generated from the unit 5 is passed through the wave transmitting vibrator 3, the sample 2 and the wave receiving vibrator 4 to the unit 6. The time arriving at the unit 6 after the generation of the longitudinal wave is measured. This time is converted to a ultrasonic wave propagation rate of the sample. The propagation rates along the machine and cross directions are, respectively, measured. The fiber orientation ratio is determined from the propagation rates along the machine and cross directions according to the ultrasonic wave propagation rate method of the substrate. In the figure, reference numeral 7 indicates an operator element and reference numeral 8 indicates a display element.

As stated hereinbefore, in order to suitably control the difference in the shrinking rate between the printing surface layer and the non-printing surface layer within a range of ±0.1%, the substrate is coated, at a side opposite to the printing surface layer of the substrate, a coating composition similar to that used to form the printing surface layer or a water-soluble resin as used as one component in the coating composition in a predetermined amount. Preferably, the water-soluble resin is coated.

The water-soluble resins useful for this purpose preferably include those used to form the coating composition and such resins may be used singly or in combination. The amount of the water-soluble resin is in the range of from 0.5 to 2 g/m$^2$, preferably from 0.7 to 1.5 g/m$^2$. If the amount is less than 0.5 g/m$^2$, a substantial degree of curling takes place. In contrast, when the amount exceeds 2 g/m$^2$, curling toward the side of the non-printing surface layer becomes considerably, with the attendant problem that runnability may be impeded. In addition, the printing paper undesirably increases in basis weight.

The printing paper of the invention is suitably applicable to known ink jet printing methods using aqueous inks and has a difference in shrinking rate between the printing surface layer and the non-printing surface layer within a range of ±0.1%. By this, when printed, the paper suffers only a reduced degree of curling or ruggedness. Moreover, the paper has a reduced contact with a printing head on printing, eventually leading to a good appearance and good handling properties of the paper after printing. In addition, the images formed on the paper are good at color development of an ink, clarity and resolution. Since the amount of the coating layer is so small that the production costs are low but the coating layer has good strength. The paper of the invention is close in touch and appearance to ordinary paper.

The invention is more particularly described by way of examples, which should not be construed as limiting the invention thereto. Comparative examples are also shown.

EXAMPLE 1

LBKP which had been beaten to a freeness of 500 m, C. S. F. was provided as a pulp for paper substrate, to which 10 wt % of precipitated calcium carbonate (TP121 of Okutama Kogyo. Co., Ltd.) was added along with 0.04 wt % of an alkylketene dimer sizing agent (Saireen 70 of Kao Corporation), followed by a paper-making process under conditions which were so set that the basis weight was 80 g/m$^2$, an apparent density was 0.80 g/cm$^3$ and the fiber orientation ratio (T/Y) determined by the ultrasonic wave propagation rate method was 1.1, thereby obtaining a paper substrate.

Thereafter, a coating composition having the following formulation was coated onto one side of the substrate in an amount of 7 g/m$^2$ to form a printing surface layer.
(1) Finely divided synthetic amorphous silica (BET specific surface area of 300 m$^2$/g Mizukasil P-78D of Mizusawa Industrial Chemicals, Ltd.) . . . 72 wt %
(2) Silanol group-modified vinyl alcohol copolymer (PVA 2130 of Kuraray Co., Ltd.) . . . 23 wt %
(3) Waterproofing agent (Epomin P1000 of Nippon Shokubai Kagaku Kogyo Co., Ltd.) . . . 5 wt %

Subsequently, a fully saponified polyvinyl alcohol (PVA 117 of Kuraray Co., Ltd.) was coated onto a side opposite to the side of the printing surface layer in an amount of 1.2 g/m$^2$ to obtain a printing paper of Example 1 which was in a completely curling-free condition.

EXAMPLE 2

The same materials as used for the substrate in Example 1 was subjected to a paper-making process under conditions which were so set that the basis weight was 80 g/m$^2$, an apparent density was 0.80 g/cm$^3$ and the fiber orientation ratio (T/Y) determined by the ultrasonic wave propagation rate method was 1.1, thereby obtaining a paper substrate.

In the same manner as in Example 1, the coating composition was applied onto the printing side of the substrate in an amount of 7 g/m$^2$, and the opposite side of the substrate was subjected to steam humidification to obtain a printing paper of Example 2 which was in a completely curling-free condition.

EXAMPLE 3

The same materials as used for the substrate in Example 1 was subjected to a paper-making process under conditions which were so set that the basis weight was 80 g/m$^2$, an apparent density was 0.80 g/cm$^3$ and the fiber orientation ratio (T/Y) determined by the ultrasonic wave propagation rate method was 1.35, thereby obtaining a paper substrate.

In the same manner as in Example 1, the coating composition was applied onto the printing side of the substrate in an amount of 7 g/m$^2$, and the opposite side of the substrate was subjected to steam humidification to obtain a printing paper of Example 3 which was in a completely curling-free condition.

EXAMPLE 4

The same materials as used for the substrate in Example 1 was subjected to a paper-making process under conditions which were so set that the basis weight was 80 g/m$^2$, an apparent density was 0.80 g/cm$^3$ and the fiber orientation ratio (T/Y) determined by the ultrasonic wave propagation rate method was 1.35, thereby obtaining a paper substrate.

In the same manner as in Example 1, the coating composition was applied onto the printing side of the substrate in an amount of 7 g/m$^2$, and 1.2 g/m$^2$ of polyvinyl alcohol was coated on the opposite side of the substrate to obtain a printing paper of Example 4 which was in a completely curling-free condition.

EXAMPLE 5

The same materials as used for the substrate in Example 1 was subjected to a paper-making process under conditions which were so set that the basis weight was 80 g/m$^2$, an apparent density was 0.80 g/cm$^3$ and the fiber orientation ratio (T/Y) determined by the ultrasonic wave propagation rate method was 1.35, thereby obtaining a paper substrate.

In the same manner as in Example 1, the coating composition was applied onto the printing side of the substrate in an amount of 7 g/m$^2$ and 1.2 g/m$^2$ of cationized starch (CATO15 of Oji National Co., Ltd.) was coated on the opposite side of the substrate to obtain a printing paper of Example 5 which was in a completely curling-free condition.

EXAMPLE 6

The same materials as used for the substrate in Example 1 was subjected to a paper-making process under conditions which were so set that the basis weight was 80 g/m$^2$, an apparent density was 0.80 g/cm$^3$ and the fiber orientation ratio (T/Y) determined by the ultrasonic wave propagation rate method was 1.35, thereby obtaining a paper substrate.

In the same manner as in Example 1, the coating composition was applied onto the printing side of the substrate in an amount of 7 g/m$^2$, and 1.2 g/m$^2$ of carboxymethylcellulose (CMC1105 of Daicel Chemical Industries, Ltd.) was coated on the opposite side of the substrate to obtain a printing paper of Example 6 which was in a completely curling-free condition.

EXAMPLE 7

The same materials as used for the substrate in Example 1 was subjected to a paper-making process under conditions which were so set that the basis weight was 80 g/m$^2$, an apparent density was 0.80 g/cm$^3$ and the fiber orientation ratio (T/Y) determined by the ultrasonic wave propagation rate method was 1.5, thereby obtaining a paper substrate.

In the same manner as in Example 1, the coating composition was applied onto the printing side of the substrate in an amount of 7 g/m$^2$, and 1.2 g/m$^2$ of polyvinyl alcohol was coated on the opposite side of the substrate to obtain a printing paper of Example 7 which was in a completely curling-free condition.

EXAMPLE 8

The same materials as used for the substrate in Example 1 was subjected to a paper-making process under conditions which were so set that the basis weight was 80 g/m$^2$, an apparent density was 0.80 g/cm$^3$ and the fiber orientation ratio (T/Y) determined by the ultrasonic wave propagation rate method was 1.35, thereby obtaining a paper substrate.

In the same manner as in Example 1, the coating composition was applied onto the printing side of substrate in an amount of 4 g/m$^2$, and 1.0 g/m$^2$ of polyvinyl alcohol was coated on the opposite side of the substrate to obtain a printing paper of Example 8 which was in a completely curling-free condition.

EXAMPLE 9

The same materials as used for the substrate in Example 1 was subjected to a paper-making process under conditions which were so set that the basis weight was 80 g/m$^2$, an apparent density was 0.80 g/cm$^3$ and the fiber orientation ratio (T/Y) determined by the ultrasonic wave propagation rate method was 1.2, thereby obtaining a paper substrate.

In the same manner as in Example 1, the coating composition was applied onto the printing side of the substrate in an amount of 10 g/m$^2$, and the opposite side of the substrate was subjected to humidification with steam to obtain a printing paper of Example 9 which was in a completely curling-free condition.

EXAMPLE 10

The same materials as used for the substrate in Example 1 was subjected to a paper-making process under conditions which were so set that the basis weight was 80 g/m$^2$, an apparent density was 0.80 g/cm$^3$ and the fiber orientation ratio (T/Y) determined by the ultrasonic wave propagation rate method was 1.35, thereby obtaining a paper substrate.

In the same manner as in Example 1, the coating composition was applied onto the printing side of the substrate in an amount of 10 g/m$^2$, and the opposite side was subjected to humidification with steam to obtain a printing paper of Example 10 which was in a completely curling-free condition.

Comparative Example 1

The same materials as used for the substrate in Example 1 was subjected to a paper-making process under conditions which were so set that the basis weight was 80 g/m$^2$, an apparent density was 0.80 g/cm$^3$ and the fiber orientation ratio (T/Y) determined by the ultrasonic wave propagation rate method was 1.40, thereby obtaining a paper substrate.

In the same manner as in Example 1, the coating composition was applied onto the printing side of the substrate in an amount of 7 g/m$^2$, and the opposite side was subjected to humidification with steam to obtain a printing paper of Comparative Example 1 which was in a completely curling-free condition.

Comparative Example 2

The same materials as used for the substrate in Example 1 was subjected to a paper-making process under conditions which were so set that the basis weight was 80 g/m$^2$, an apparent density was 0.80 g/cm$^3$ and the fiber orientation ratio (T/Y) determined by the ultrasonic wave propagation rate method was 1.60, thereby obtaining a paper substrate.

In the same manner as in Example 1, the coating composition was applied onto the printing side of the substrate in an amount of 7 g/m$^2$, and the opposite side was subjected to humidification with steam to obtain a printing paper of Comparative Example 2 which was in a completely curling-free condition.

Comparative Example 3

The same materials as used for the substrate in Example 1 was subjected to a paper-making process under conditions which were so set that the basis weight was 80 g/m², an apparent density was 0.80 g/cm³ and the fiber orientation ratio (T/Y) determined by the ultrasonic wave propagation rate method was 1.40, thereby obtaining a paper substrate.

In the same manner as in Example 1, the coating composition was applied onto the printing side of the substrate in an amount of 10 g/m², and the opposite side was subjected to humidification with steam to obtain a printing paper of Comparative Example 3 which was in a completely curling-free condition.

Comparative Example 4

The same materials as used for the substrate in Example 1 was subjected to a paper-making process under conditions which were so set that the basis weight was 80 g/m², an apparent density was 0.80 g/cm³ and the fiber orientation ratio (T/Y) determined by the ultrasonic wave propagation rate method was 1.35, thereby obtaining a paper substrate.

In the same manner as in Example 1, the coating composition was applied onto the printing side of the substrate in an amount of 3 g/m², and the opposite side was subjected to coating with 0.9 g/m² of polyvinyl alcohol to obtain a printing paper of Comparative Example 4 which was in a completely curling-free condition.

Comparative Example 5

The same materials as used for the substrate in Example 1 was subjected to a paper-making process under conditions which were so set that the basis weight was 80 g/m², an apparent density was 0.80 g/cm³ and the fiber orientation ratio (T/Y) determined by the ultrasonic wave propagation rate method was 1.35, thereby obtaining a paper substrate.

In the same manner as in Example 1, the coating composition was applied onto the printing side of the substrate in an amount of 11 g/m², and the opposite side was subjected to coating with 1.4 g/m² of polyvinyl alcohol to obtain a printing paper of Comparative Example 5 which was in a completely curling-free condition.

The recording papers obtained in the examples and the comparative examples were subjected to measurement of a difference in shrinking rate according to the following method.

Each recording paper was cut along the cross direction into sample pieces having a length of 100 mm and a width of 50 mm. Each sample was split into substantially halves including a printing surface layer and a non-printing surface layer using a sheet splitter of Kumagaya Riki Ind. Co., Ltd. At the time, a double-sided self-adhesive tape was attached to at the tip of the sample paper on opposite sides thereof for splitting into the two layers. The shrinking rate of each of the divided printing surface layer and non-printing surface layer along the cross direction was measured under such conditions as set out hereinbefore by use of an HK-type shrinkage tester of Shinko Electric Co., Ltd., to determine a difference by subtracting the shrinking rate value of the non-printing surface layer from that of the printing surface layer.

Each sample was further subjected to measurements of a degree of curling, image quality and coating strength. With regard to the image quality, the clarity of color development and the resolution were assessed. The results of the assessment of the printing papers of Examples 1 to 10 are shown in Table 1 and the results of the assessment of Comparative Examples 1 to 5 are shown in Table 2.

The degree of curling was evaluated in the following manner. Each sample was subjected to moisture conditioning under conditions of 20° C. and 65% R.H. for 3 hours or over and then to printing over the entire surface of the printing surface layer of the sample at a coverage of 50%. The printed sample was placed on a flat plate and the ink was completely dried, followed by measuring the height of the sample at the four corners thereof from the plate by means of a slide caliper. A maximum value of the four measurements was taken as a degree of curling. The assessment was made by four ranks including "very small" for a height of curling smaller than 0.5 cm, "small" for a height of from 0.5 cm to smaller than 1 cm, "moderate" for a height of from 1 cm to smaller than 2 cm, and "considerable" for a height of not smaller than 2 cm.

The image quality was evaluated in the following manner: there was used a printer having four printing heads for black, cyan, magenta and yellow colors and having the capability of a 300 dpi printing density and there was also used an ink having a viscosity of 1 to 8 cps., and a surface tension of 40 dynes/cm or below.

The clarity for color development was evaluated according to the following four ranks after confirmation of a formed color image through visual observation: ⊙ for "very good", ○ for "good", Δ for "moderate" and x for "poor".

The resolution was evaluated according to the following four ranks by printing characters "" and "" on each sample by use of a 8-point Ming-type style and judging their intelligibility and dignity through visual observation: ⊙ "very good for both intelligibility and dignity", ○ for "good for both intelligibility and dignity", Δ for "slightly deformed in the printed characters" and x for "substantially deformed in the printed characters"

The coating strength of the coating layer of the sample paper was evaluated according to the following four ranks: a sample paper was-folded and rolled with 2 kg of a metallic roll at the folded portion whereupon the separation of the coating layer was assessed as ⊙ for "not separated at all", ○ for "slightly separated", Δ "moderately separated", and x "substantially separated".

TABLE 1

|  | Example 1 | Example 2 | Example 3 | Example 4 | Example 5 | Example 6 | Example 7 | Example 8 | Example 9 | Example 10 |
| --- | --- | --- | --- | --- | --- | --- | --- | --- | --- | --- |
| Difference in Shrinking Rate (%) | 0 | 0.03 | 0.10 | 0.06 | 0.08 | 0.08 | 0.09 | 0.06 | −0.05 | −0.10 |
| T/Y Ratio of Substrate | 1.10 | 1.10 | 1.35 | 1.35 | 1.35 | 1.35 | 1.50 | 1.35 | 1.20 | 1.35 |
| Water-soluble Resin in Printing Surface Coating | Silanol group-modified | Silanol group-modified | Silanol group-modified | Silanol group-modified | Silanol group-modified | Silanol group-modified | Silanol group-modified | Silanol group-modified | Silanol group-modified | Silanol group-modified |

TABLE 1-continued

|  | Example 1 | Example 2 | Example 3 | Example 4 | Example 5 | Example 6 | Example 7 | Example 8 | Example 9 | Example 10 |
|---|---|---|---|---|---|---|---|---|---|---|
| Material in Non-printing surface Coating | PVA Fully saponified PVA | PVA Nil | PVA Nil | PVA Fully saponified PVA | PVA Starch | PVA CMC | PVA Fully saponified PVA | PVA Fully saponified PVA | PVA Nil | PVA Nil |
| Coating Amount of Printing Layer (g/m$^2$) | 7 | 7 | 7 | 7 | 7 | 7 | 7 | 4 | 10 | 10 |
| Degree of Curling after Printing (mm) | Very small | Very small | Small | Small | Small | Small | Small | Small | Very small | Small |
| Color Development | ⊙ | ⊙ | ⊙ | ⊙ | ⊙ | ⊙ | ⊙ | ○ | ⊙ | ⊙ |
| Resolution | ⊙ | ⊙ | ⊙ | ⊙ | ⊙ | ⊙ | ⊙ | ○ | ⊙ | ⊙ |
| Coating Strength | ⊙ | ⊙ | ⊙ | ⊙ | ⊙ | ⊙ | ⊙ | ⊙ | ○ | ○ |

TABLE 2

|  | Comparative Example 1 | Comparative Example 2 | Comparative Example 3 | Comparative Example 4 | Comparative Example 5 |
|---|---|---|---|---|---|
| Difference in Shrinking Rate (%) | 0.11 | 1.16 | −0.11 | 0.06 | −0.07 |
| T/Y Ratio of Substrate | 1.40 | 1.60 | 1.40 | 1.35 | 1.35 |
| Water-soluble Resin in Printing Surface Coating | Silanol group-modified PVA | Silanol group-modified PVA | Silanol group-modified PVA | Silanol group-modified PVA | Silanol group-modified PVA |
| Material in Non-printing Surface Coating | Nil | Nil | Nil | Fully saponified PVA | Fully saponified PVA |
| Coating Amount of Printing Layer (g/m$^2$) | 7 | 7 | 10 | 3 | 11 |
| Degree of Curling After Printing (mm) | Moderate | Considerable | Moderate | Small | Small |
| Color Development | ⊙ | ⊙ | ⊙ | X | ⊙ |
| Resolution | ⊙ | ⊙ | ⊙ | X | ⊙ |
| Coating Strength | ⊙ | ⊙ | ○ | ⊙ | X |

Figure 2:
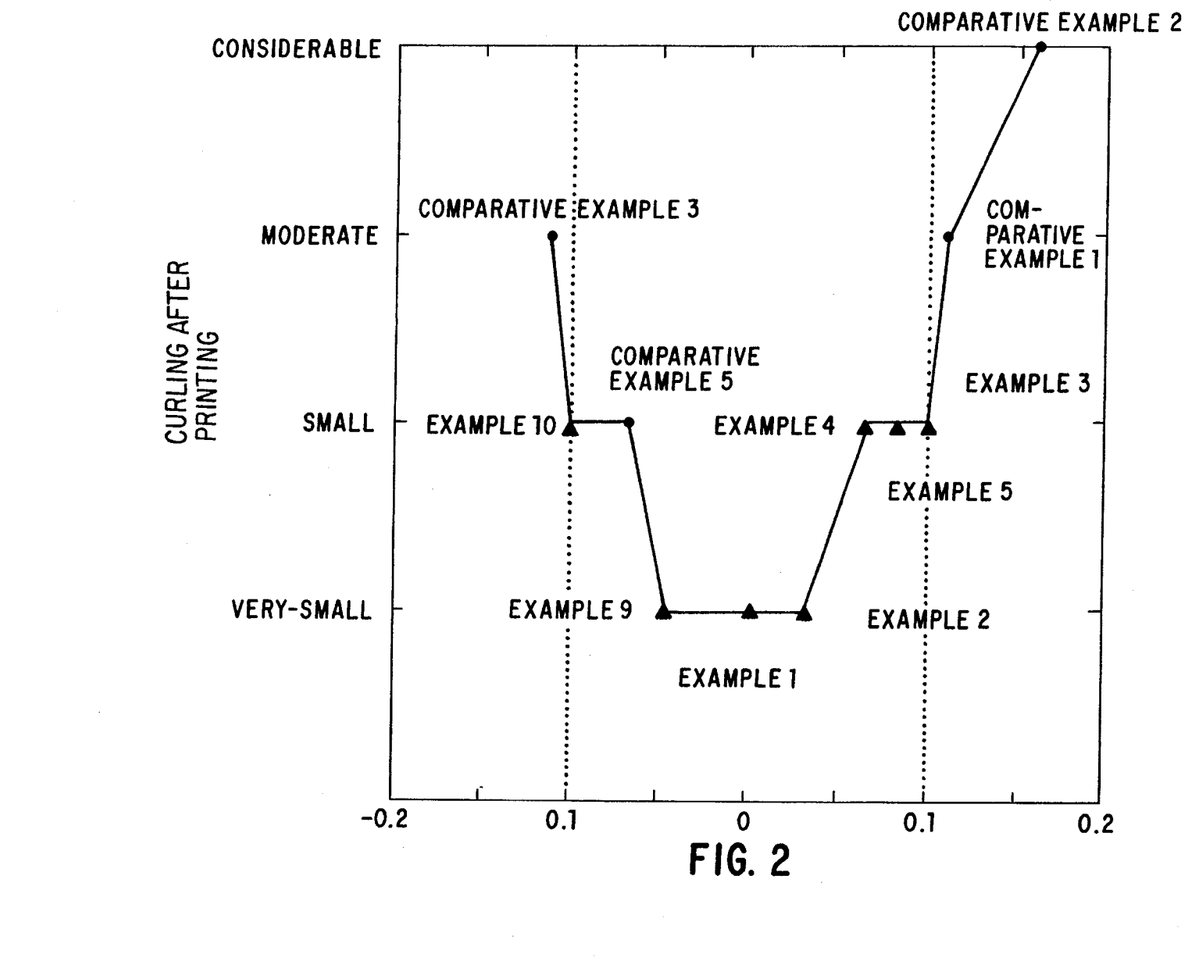
FIG. 2 is a graphical representation showing the relation of the degree of curling in variation of the difference in shrinking rate between the printing surface layer and the non-printing surface layer for printing paper sheets obtained in Examples 1 to 5, 9 and 10 and Comparative Examples 1 to 3 and 5.

The difference in the shrinking rate between the printing surface layer and the non-printing surface layer for the printing papers of Examples 1 to 5, 9 and 10 and Comparative Examples 1 to 3 and 5 are shown in FIG. 2.

As will be apparent from the results of Tables 1 and 2 and FIG. 2, the degree of curling or ruggedness of the printing paper sheets of the invention are significantly smaller than that of the printing paper sheets for comparison, ensuring good clarity for the color development and resolution. Since the coating amount is so small, the coating strength is very good. The printing sheets of the invention are low in production cost and can be provided like ordinary paper.

What is claimed is:

1. A printing paper which comprises a paper substrate and a coating layer formed on at least one side of said paper substrate in an amount of from 4 to 10 g/m$^2$ and formed from a coating composition which comprises a white pigment and a water-soluble resin, wherein when the paper sheet is divided or split into a printing surface layer which consists of a portion covering substantially from a center line of the total thickness of said printing paper to the surface of the coating layer and a non-printing surface layer which consists of a portion covering substantially said center line to a surface of a side opposite to the side of the coating layer, a difference in shrinking rate along a cross direction in a paper-making process between the printing surface layer and the non-printing surface layer is within a range of ±0.1% wherein the shrinking rate is a dimensional variation rate of the printing surface layer and the non-printing surface layer which occurs when changing conditions of 20° C. and 90% R.H. to 20° C. and 25% R.H.

2. A printing paper according to claim 1, wherein said paper substrate has an orientation ratio between the fibers arranged along the machine and cross directions in a paper-making process, which is determined according to a ultrasonic wave propagation rate method, is not greater than 1.35.

3. A printing paper according to claim 1, wherein said paper substrate has an apparent density ranging from 0.70 to 0.90 g/cm$^3$.

4. A printing paper according to claim 1, wherein said paper substrate has a basis weight of from 50 to 100 g/m$^2$ and a thickness of from 65 to 150 μm.

5. A printing paper according to claim 1, wherein said coating layer is formed on one side of said paper substrate.

6. A printing paper according to claim 1, wherein said coating layer is formed on both sides of said paper substrate.

7. A printing paper according to claim 1, wherein said water-soluble resin consists essentially of a member selected from the group consisting of vinyl alcohol polymers.

8. A printing paper according to claim 7, wherein said water-soluble resin consists essentially of a silanol group-modified vinyl alcohol copolymer.

9. A printing paper according to claim 1, wherein said white pigment has a BET specific surface area of from 100 to 400 m$^2$/g and an average size of from 2 to 15 μm.

10. A printing paper according to claim 9, wherein said white pigment consists essentially of amorphous silica and is present in an amount of from 50 to 85 wt % of the coating composition.

11. A printing paper according to claim 1, further comprising a coating of a water-soluble resin on a side of said paper substrate opposite to the coating layer when said coating layer is formed on one side of said paper substrate.

12. A printing paper according to claim 11, wherein said water-soluble resin consists essentially of a member selected from the group consisting of vinyl alcohol polymers.

13. A printing paper according to claim 12, wherein said water-soluble resin consists essentially of a silanol group-modified vinyl alcohol copolymer.

14. A printing paper according to claim 11, wherein said water-soluble resin is formed in an amount of from 0.5 to 2 g/m$^2$.

* * * * *